US008642527B2

(12) United States Patent
van Buskirk et al.

(10) Patent No.: US 8,642,527 B2
(45) Date of Patent: Feb. 4, 2014

(54) OXIDIZING BLEACH COMPOSITION

(75) Inventors: Gregory van Buskirk, Danville, CA (US); Scott Cumberland, Pleasanton, CA (US); Thomas W. Kaaret, Alamo, CA (US); William L. Smith, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 1591 days.

(21) Appl. No.: 11/764,621

(22) Filed: Jun. 18, 2007

(65) Prior Publication Data

US 2012/0115767 A1    May 10, 2012

(51) Int. Cl.
*C11D 7/60* (2006.01)
(52) U.S. Cl.
USPC ............ 510/310; 510/303; 510/418; 510/370
(58) Field of Classification Search
USPC .................................. 510/310, 303, 418, 370
See application file for complete search history.

(56) References Cited

U.S. PATENT DOCUMENTS

| | | | |
|---|---|---|---|
| 4,017,476 A | 4/1977 | Murray et al. | |
| 4,271,030 A | 6/1981 | Brierley et al. | |
| 4,457,855 A | 7/1984 | Sudbury et al. | |
| 4,474,677 A | 10/1984 | Foxlee | |
| 4,486,237 A | 12/1984 | Paffoni et al. | |
| 4,623,476 A | 11/1986 | Nayar et al. | |
| 4,708,816 A * | 11/1987 | Chang et al. | 252/186.25 |
| 4,714,562 A | 12/1987 | Roselle et al. | |
| 4,917,814 A * | 4/1990 | MacIntyre et al. | 510/373 |
| 4,931,207 A | 6/1990 | Cramer et al. | |
| 4,952,333 A | 8/1990 | Cramer | |
| 5,089,162 A | 2/1992 | Rapisarda et al. | |
| 5,104,571 A | 4/1992 | Cramer | |
| 5,106,421 A | 4/1992 | Marshall, Jr. et al. | |
| 5,470,502 A | 11/1995 | Hahn et al. | |
| 5,679,661 A * | 10/1997 | Willey | 514/63 |
| 5,688,435 A | 11/1997 | Chang et al. | |
| 5,710,197 A | 1/1998 | Fischer et al. | |
| 5,795,379 A | 8/1998 | Schwenk et al. | |
| 5,871,872 A | 2/1999 | Matijevic et al. | |
| 6,228,824 B1 | 5/2001 | Gorlin | |
| 6,258,764 B1 | 7/2001 | Gorlin | |
| 6,420,328 B1 | 7/2002 | Gorlin | |
| 6,448,215 B1 | 9/2002 | Grande et al. | |
| 6,503,877 B2 | 1/2003 | Grande et al. | |
| 6,624,134 B1 | 9/2003 | Briatore et al. | |
| 6,727,317 B2 | 4/2004 | Kurja et al. | |
| 6,774,096 B1 * | 8/2004 | Paye | 510/130 |
| 6,872,444 B2 * | 3/2005 | McDonald et al. | 428/206 |
| 6,921,743 B2 | 7/2005 | Scheper et al. | |
| 2004/0127393 A1 * | 7/2004 | Valpey et al. | 510/511 |
| 2004/0156986 A1 | 8/2004 | Yadav | |
| 2005/0075453 A1 | 4/2005 | Mathauer et al. | |
| 2006/0055316 A1 | 3/2006 | Wu et al. | |
| 2006/0096614 A1 * | 5/2006 | Krisko | 134/6 |
| 2009/0007936 A1 * | 1/2009 | Uhl et al. | 134/6 |

FOREIGN PATENT DOCUMENTS

| | | |
|---|---|---|
| WO | WO 99/40123 A2 | 8/1999 |
| WO | WO 00/50554 A1 | 8/2000 |
| WO | WO2007 054126 * | 5/2007 |

OTHER PUBLICATIONS

Clemens et al, Nanocolorants—Pigments with Dyestuff Properties, Polymer Preprints 41(1), pp. 24-25 (2000).

* cited by examiner

*Primary Examiner* — Mark Eashoo
*Assistant Examiner* — M. Reza Asdjodi
(74) *Attorney, Agent, or Firm* — Stacy H. Combs (57) ABSTRACT

The invention provides an aqueous bleaching solution for substrate treatment. The aqueous bleaching solution features a source of oxidant and a plurality of optically functional nanoparticles. The optically functional nanoparticles are nanoparticles in the range of about 0.1 nanometers to about 400 nanometers in size. The aqueous bleaching solution may optionally include one or more an oxidant-stable surfactants and optionally, one or more oxidant-stable polymers, and adjuncts. The optically functional nanoparticles are extremely stable in the aqueous bleaching solution and remain substantially suspended in the aqueous bleaching solution due to their extremely small size despite having an average density greater than that of the bleaching solution. The optically functional nanoparticles provide at least one optical functional benefit to the bleaching solution owing to their uniform and stable suspension throughout the solution, including such benefits as uniform light absorption, light and radiation scattering, fluorescent emission, phosphorescent emission, coloration, and visual aesthetic benefits and the like. Further, optically functional benefits include those benefits provided to a substrate or surface treated with the aqueous bleaching solutions whereby the optically functional property is transferred either temporarily or permanently to the substrate or surface following contact with bleaching solutions containing the optically functional nanoparticles.

2 Claims, 2 Drawing Sheets

OXIDIZING BLEACH COMPOSITION

BACKGROUND OF THE INVENTION

1. Field of the Invention

The invention relates generally to the field of substrate treating, and more specifically, to aqueous bleaching solutions with optically functional nanoparticles for providing functional benefits to the bleaching solution and/or a treated substrate, wherein the optically functional nanoparticles are stable to degradation and settling in the aqueous bleaching solutions.

2. Description of the Related Art

Bleaches are used for cleaning purposes such as stain removal, whitening, disinfecting, sanitizing, sterilizing, and the like. Bleaches may also be used during laundering to bleach stubborn stains and dirt, as well as to achieve whitening and brightening of fabrics, particularly of white and light-colored textiles and materials. Conventional bleaches include an aqueous solution of an oxidant such as sodium hypochlorite, coloring agents, whiteners, and the like.

However, ensuring that a stable and visually pleasing color is achieved in an aqueous bleaching solution containing an oxidant is difficult. This may be attributed to the fact that particulate materials such as dyes, pigments and whiteners either degrade due to oxidation or do not form stable dispersions and settle out of solution.

Existing methods for providing a stable aqueous bleaching solution include the use of oxidation-resistant pigments and dyes, either alone or encapsulated. Examples of these oxidation-resistant pigments include inorganic pigments such as tramline blue (UMB), cobalt blue, iron oxide, and the like. These pigments are chemically compatible with the oxidants but they do not form stable dispersions and settle out of solution quickly. Hence, the aqueous bleaching solutions containing these pigments require the use of thickening agents and flocculants to form gel-like structures to suspend these pigments. Further, the encapsulation of these pigments, with subsequent dispersion in the source of oxidant necessitates a careful balancing of densities and electrostatic charges in order to resist precipitation and particle agglomeration in the aqueous bleaching solutions. U.S. Pat. Nos. 6,420,328, 6,448,215, 6,503,877, 6,624,134, 5,688,435, 4,708,816, 4,931,207, 4,952,333, 5,104,571, 4,623,476, 4,271,030 describe the use of such pigments and are herein incorporated in their entirety as references.

Existing methods also suggest the use of certain water-soluble inorganic compounds such as chromium or permanganate salts, which are compatible with the oxidants, to impart color to the aqueous bleaching solutions. These water-soluble inorganic compounds may be used to form yellow or purple solutions. However, aqueous bleaching solutions containing these inorganic compounds do not have the desired aesthetics.

U.S. Pat. Nos. 4,714,562 and 5,089,162 disclose dyes for use in liquid dishwasher detergents that have less than 3 percent sodium hypochlorite and high concentrations of builders and other ingredients. However, such dyes have limited utilization to simply increasing the yellow color of the aqueous bleaching solutions.

U.S. Pat. No. 4,474,677 describes halogenated copper phthalocyanine pigments for forming blue or green aqueous bleaching solutions. However, the stability of the blue bleaching solutions is rather limited. These halogenated copper phthalocyanine pigments release copper ions when they degrade, which tend to catalyze the decomposition of the sodium hypochlorite present in the aqueous bleaching solutions so that the resulting blue bleaching solutions do not have an adequate shelf life for a consumer product, and the formation of the blue bleaching solutions requires a dispersion agent to hinder precipitation.

Other existing methods achieve stable aqueous bleaching solutions by increasing the viscosities of these aqueous bleaching solutions. These methods aim at attaining a rheology that imparts elasticity or a false body to the aqueous bleaching solutions. However, these measures are temporary and are subject to chemical instability at higher levels of oxidants. Further, additives such as surfactant blends and polymer thickeners used to increase the viscosity may not be desirable, when, for example, a residue is not desired or the aqueous bleaching solutions are used for disinfecting food surfaces.

Colorants are normally understood in the art to include both pigments and dyestuff. Pigments refer mainly to inorganic salts and oxides, such as iron and chromium oxides, which are usually dispersed in crystal or powder form in an application medium. The color properties of the dispersion depends on the particle size and form of the pigment. Pigment colorants tend to be highly durable, heat stable, solvent resistant, lightfast, and migration fast. On the other hand, they also tend to be hard to process and have poor color brilliance and strength.

Dyes (also called dyestuffs) are conventionally understood to refer to organic molecules dissolved, as molecular chromophores, in the application medium. Examples are azo dyes, coumarin dyes, and perylene dyes. The color imparted by dyestuff to the resulting solution depends on the electronic properties of the chromophore molecule. Dyestuff colorants tend to have excellent brilliance and color strength, and are typically easy to process, but also have poor durability, poor heat and solvent stability, and high migration. They are also poorly bleach resistant being organic molecules bearing oxidant susceptible chemical groups, and generally fail to provide long lasting benefits to bleaching solutions.

Because of the contrasting properties of both types of colorants, much work has been done trying to improve the attributes of each class of colorant (see, for example, U.S. Pat. Nos. 4,017,476, 5,470,502, 5,710,197, 5,795,379, 5,871,872) and to combine the advantages of both into a single product (U.S. Pat. Nos. 4,486,237, 5,106,421, and PCT Publication WO 99/40123). These prior-art improvements have often involved binding dyes in a polymeric matrix to achieve greater color durability, improved heat and solvent stability, and to reduce migration as a result of the stable structure provided by the matrix.

More recently, U.S. Pat. No. 6,921,743 has described the use of some nanoparticles in combination with automatic dishwashing compositions where a halogen dioxide salt is electrolytically generated at time of use. However the materials are selected for suitability regarding surface modification of ceramic surfaces.

U.S. Pat. Pub. 2004/40156986 describes the use of colored nanopigments to provide a means for coloring compositions of matter that exhibit greater transparency than a coarse colored pigment, particularly in the visible wavelength range. However, the nanopigments employed are only adapted for use by incorporation into solid materials such as plastic, ceramic, cement, glass, wood, fibers, or in thickened coating materials such as paint and ink to be applied to a material surface in the form of a macroscopic film of the colored composition of matter.

In light of the foregoing discussion, there is a need for an aqueous bleaching solution that can be optically modified in a stable manner and that performs the functions of bleaching, whitening, brightening, and the like. The aqueous bleaching solution needs to include a stable dispersion an optically modifying material, and needs to be resistant to aggregation and settling. Further, the optically modified aqueous bleaching solution should be stable without the use of thickening agents, flocculants and dispersing agents.

SUMMARY OF THE INVENTION

An object of the invention is to provide a stable aqueous bleaching solution that has been optically modified to provide at least one optically functional benefit obtained by incorporation of optically functional nanoparticles.

Another object of the invention is to provide a stable aqueous bleaching solution with optically functional nanoparticles providing at least one optically functional benefit to the solution or substrates treated therewith, where the bleaching solution can be formulated without using thickening agents, flocculants and dispersing agents.

Another object of the invention is to provide a stable aqueous bleaching solution of optically functional nanoparticles which serve the function of providing at least one optically functional benefit to the bleach solution or substrate treated therewith, such optically functional benefits including that of uniform light absorption, light and radiation scattering, fluorescent emission, phosphorescent emission, coloration, and visual aesthetic benefits and the like.

In accordance with the above objects and those that will be mentioned and will become apparent below, an embodiment of the invention provides an aqueous bleaching solution with optically functional nanoparticles for substrate treatment.

Further features and advantages of the present invention will become apparent to those with ordinary skill in the art, in view of the detailed description of the collective embodiments below, when considered together with the attached claims.

DETAILED DESCRIPTION

Before describing the present invention in detail, it is to be understood that this invention is not limited to particularly exemplified systems, compositions or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "solution" may include two or more such solutions.

Unless defined otherwise, all technical and scientific terms used herein have the same meaning as commonly understood by one with ordinary skill in the art to which the invention pertains. Although a number of methods and materials, similar or equivalent to those described herein, can be used in the practice of the present invention, some of the preferred materials and methods are described herein.

In the present application, effective amounts are generally those amounts listed as the ranges or levels of ingredients in the descriptions, which follow hereto. Unless otherwise stated, amounts listed in percentage ("%" or "percent") are in weight percent (based on 100% active) of the total composition.

It may be noted that the term "bleaching", as used in this document, may also refer to processes such as "cleaning", "whitening", "brightening", and the like. All these terms have also been used somewhat interchangeably to denote overall improved cleanliness and whiteness of, for example, a washed fabric. Further, the term "hypohalite" has been used to describe both a hypohalite and a hypohalite generator, unless otherwise indicated. Also the term "hypohalous" has been used to describe a source of active halogen, including chlorine, bromine and iodine, present in the appropriate oxidation state.

In one embodiment of the invention is provided an aqueous solution for substrate cleaning comprising a source of oxidant and a plurality of optically functional nanoparticles characterized such that (i) the average density of the plurality of optically functional nanoparticles is greater than that of the aqueous solution with the source of oxidant present, and (ii) the average particle size of the plurality of optically functional nanoparticles is between 0.1 nanometers to about 400 nanometers; optionally, an oxidant-stable polymer; optionally, an oxidant-stable surfactant; and water; wherein said plurality of optically functional nanoparticles are oxidant-stable in the aqueous solution; and wherein the average density of said plurality of optically functional nanoparticles is greater than 1.15 grams per cubic centimeter.

In another embodiment of the invention is provided an aqueous solution for substrate cleaning comprising a source of oxidant and a plurality of optically functional nanoparticles characterized such that (i) the average density of the plurality of optically functional nanoparticles is greater than that of the aqueous solution with the source of oxidant present, and (ii) the average particle size of the plurality of optically functional nanoparticles is between 0.1 nanometers to about 400 nanometers; optionally, an oxidant-stable polymer; optionally, an oxidant-stable surfactant; and water; wherein said plurality of optically functional nanoparticles are oxidant-stable in the aqueous solution; and wherein the average density of said plurality of optically functional nanoparticles is greater than 1.15 grams per cubic centimeter; and wherein said plurality of optically functional nanoparticles comprise materials selected from $Co_xAl_yO_z$, $Co_xB_yO_z$, $Co_xZn_yO_z$, $Co_xZn_yB_zO_w$, $Co_xZn_ySi_zO_w$. $Co_xCr_yO_z$, $Co_xMg_y$-$B_zO_w$, chrome antimony titanium buff rutile, chrome tungsten titanium buff rutile, cobalt aluminate blue spinel, cobalt chromite spinel, cobalt nickel zinc titanium spinel, copper manganese chromite black spinel, chromium oxide, manganese antimony chromite titanium buff rutile, manganese zinc chromate spinel, nickel antimony titanium rutile, nickel tungsten rutile, zinc chrome cobalt aluminate spinel, titanium dioxide, zinc oxide, cerium oxide, magnesium oxide, and mixtures thereof; wherein x, y, z and w are integers having independently selected values of between 1 to about 10.

In yet another embodiment of the invention, a bleaching solution is provided having a source of oxidant being an active halogen selected from the group consisting of hypohalite ion, hypohalous acid, and combinations thereof;

wherein said halogen is chlorine, bromine or iodine, in combination with a plurality of optically functional nanoparticles.

In a further embodiment of the invention, a bleaching solution is provided having a plurality of optically functional materials selected from the group consisting of pigments, dyestuffs, fluorescent agents, phosphorescent agents, fluorescent whitening agents, brighteners, ultraviolet absorbing materials, ultraviolet reflecting materials, light absorbing materials, mineral oxides, metal oxides, quantum dots, semiconductor materials, and further including polymer encapsulated derivatives thereof, and combinations thereof, wherein the plurality of optically functional nanoparticles are oxidant-stable in the aqueous solution; and wherein the average density of said plurality of optically functional nanoparticles is greater than 1.15 grams per cubic centimeter.

In a particular embodiment of the invention, suitable quantum dot materials for use as optically functional materials combined with a bleaching solution comprise those semiconductor materials selected from the group consisting of CdSe, PbS, InAs, InGaP, ZnS, ZnSe, ZnTe, CdS, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, Ge, Si, and alloys or mixtures thereof, core/shell layered materials. polymeric coated materials, and combinations thereof.

In yet another embodiment of the invention, a bleaching solution is provided having a source of oxidant, and a plurality of optically functional nanoparticles which are visibly colored particles exhibiting at least one optical absorbance band providing a human perceivable color to the aqueous solution that lies within the visible spectrum of about 300 to 800 nanometers wavelength.

In a further embodiment of the invention, an aqueous solution is provided with a source of oxidant, and a plurality of optically functional nanoparticles which exhibit an absorbance band between 250 to 400 nanometers corresponding to the absorbance maximum of an aqueous hypohalous and/or hypohalite species present as the source of oxidant.

In yet a further embodiment of the invention, an aqueous solution is provided with a source of oxidant, and a plurality of optically functional nanoparticles exhibiting at least one optical absorbance band that lies within the ultraviolet portion of the spectrum below about 300 nanometers wavelength, and providing no human perceivable color to the aqueous solution within the visible spectrum of about 300 to 800 nanometers wavelength.

One embodiment of the invention provides a method of treating a substrate comprising the steps of (1) contacting a substrate with an aqueous solution comprising a source of oxidant, a plurality of optically functional nanoparticles characterized such that the average density of the plurality of optically functional nanoparticles is greater than that of the aqueous solution with the source of oxidant present, and the average particle size of the plurality of optically functional nanoparticles is between 0.1 nanometers to about 400 nanometers; optionally, an oxidant-stable surfactant; optionally, one or more oxidant-stable polymers; and water; and (2) optionally rinsing said substrate with water; wherein said plurality of optically functional nanoparticles are oxidant-stable in the aqueous solution; wherein the average density of said plurality of optically functional nanoparticles is greater than 1.15 grams per cubic centimeter.

In other embodiments of the invention, an aqueous solution containing an oxidant source and a plurality of optically functional nanoparticles is used to treat a substrate selected from a hard surface, such as for example, but not limited to counter tops, toilets, bathroom surfaces, floors, metal surfaces, wooden surfaces; or a soft surface, such as for example, but not limited to fabrics, textiles, clothing, rugs; and combinations thereof.

In yet another embodiment of the invention is an aqueous solution for substrate cleaning comprising a source of oxidant comprising hypochlorite bleach at a solution pH of between about pH 7 to about pH 13.5; a plurality of optically functional nanoparticles characterized such that the average density of the plurality of optically functional nanoparticles is greater than that of the aqueous solution with the source of oxidant present, and the average particle size of the plurality of optically functional nanoparticles is between 0.1 nanometers to about 400 nanometers; an oxidant-stable polymer comprising a water soluble or water dispersible polymer or copolymer compound comprising one or more monomers selected from the group consisting of acrylic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, sulfoethyl acrylate, and combinations thereof; optionally, an oxidant-stable surfactant; and water; wherein said plurality of optically functional nanoparticles are oxidant-stable in the aqueous solution; wherein the average density of said plurality of optically functional nanoparticles is greater than 1.15 grams per cubic centimeter; wherein the final viscosity of the aqueous solution is less than 100 MilliPascal seconds at 25° C.; wherein said substrate is a surface comprising a household surface selected from the group consisting of counter tops, toilets, bathroom surfaces, floors, walls, metal surfaces, plastic surfaces, wooden surfaces, fabrics, textiles, clothing, rugs, and combinations thereof.

In another embodiment of the invention, there is provided a kit for substrate cleaning, the kit comprising (1) an aqueous solution for substrate treatment comprising a source of oxidant, a plurality of optically functional nanoparticles characterized such that the average density of the plurality of optically functional nanoparticles is greater than that of the aqueous solution with the source of oxidant present, and the average particle size of the plurality of optically functional nanoparticles is between 0.1 nanometers to about 400 nanometers; wherein the average density of the plurality of optically functional nanoparticles is greater than 1.15 grams per cubic centimeter; optionally, an oxidant-stable surfactant; optionally, one or more oxidant-stable polymers; and water; and (2) packaging material for packaging and dispensing of said aqueous solution; (3) instructions for applying said aqueous solution to at least one surface of a selected substrate in order to form a treated substrate; (4) instructions for a process for removing the aqueous solution from a treated substrate wherein said process for removing the aqueous solution provides a means for either (a) leaving said optically functional nanoparticles on the surface of said treated substrate; or (b) removing said optically functional nanoparticles from the surface of said treated substrate.

Source of Oxidant

The source of oxidant acts as a bleach and enables the removal of colored stains, organic stains, and produces a whitening effect on fibers. The source of oxidant also destroys malodorous molecules and kills or reduces germs, bacteria, viruses and other microorganisms. Examples of the source of oxidant may include, for example, a suitable oxidizing agent, a bleaching component, and the like.

In accordance with an embodiment of the invention, the source of oxidant may include a source of active halogen, which may include a hypohalite ion, hypohalous acid, and combinations thereof. In particular, the source of oxidant may include a hypohalite-producing species, for example, alkali metal and alkaline earth salts of hypohalites, haloamines, haloimines, haloimides, haloamides, and the like. Hypohalites display high activity at low-concentration levels and are normally aggressive to actives and adjuncts that are susceptible to the bleaching effects of the source of oxidant. Hypohalites provide good stain removal, whitening, brightening, allergen control, chemical decontamination, sanitization, sterilization, and are broad-spectrum antimicrobial agents. In accordance with an embodiment of the invention, these hypohalites may be at least partially water-soluble and may generate an active halogen ion such as an 'OCl⁻' ion on dissolution in water.

In a particular embodiment, the source of oxidant is a hypochlorite or a generator of hypochlorite in the aqueous bleaching solution, although a hypobromite or a hypobromite generator is also suitable. Examples of hypochlorite generators may include sodium hypochlorite, potassium hypochlorite, lithium hypochlorite, magnesium hypochlorite, calcium hypochlorite, chlorinated trisodium phosphate dodecahydrate, potassium and sodium dichloroisocyanurate, trichlorocyanuric acid, and the like.

In accordance with yet another embodiment of the invention, the source of oxidant may be an alkali metal hypochlorite, an alkaline earth salt of hypochlorite, or a mixture thereof. A particularly effective source of oxidant that may be employed in the invention is sodium hypochlorite with the chemical formula NaOCl.

In accordance with an embodiment of the invention, the hypohalite-generating compounds mentioned above may be employed in solid, powdered, granular, paste or tablet forms, due to their stability in essential dry form and their good mechanical processability. Further, the hypohalite may be formed by using methods well known to those skilled in the art.

In accordance with an embodiment of the invention, organic bleach sources may also be used as the source of oxidant. Examples of the organic bleach sources that are suitable for use may include heterocyclic N-bromo and N-chloro imides such as trichlorocyanuric and tribromocyanuric acid, dibromocyanuric acid and dichlorocyanuric acid, potassium and sodium salts thereof, N-brominated and N-chlorinated succinimide, malonimide, phthalimide and naphthalimide. Further, hydantoins such as dibromodimethyl-hydantoin and dichlorodimethyl-hydantoin, chlorodimethylhydantoin, N-chlorosulfamide (haloamide) and chloramine (haloamine) may also be used as the source of oxidant.

In accordance with yet another embodiment of the invention, the source of oxidant may be oxygen-based. Examples of an oxygen-based source of oxidant include a peroxygen, a peroxyhydrate, an active oxygen-generating compound, and the like. In particular, the peroxygen bleaches may include hydrogen peroxide or sources thereof. It may be noted that a source of hydrogen peroxide refers to any compound that generates active oxygen when the compound is in contact with water. Examples of suitable water-soluble sources of hydrogen peroxide, for use herein, may include percarbonates, preformed percarboxylic acids, persilicates, persulphates, perborates, organic and inorganic peroxides, hydroperoxides, and the like.

In addition, other classes of peroxides may also be used as an alternative to hydrogen peroxide and sources thereof, or in combination with hydrogen peroxide and sources thereof. Examples of such classes of peroxides include dialkylperoxides, diacylperoxide, performed percarboxylic acids, organic and inorganic peroxides, hydroperoxides, and the like. Suitable organic peroxides/hydroperoxides may include diacyl and dialkyl peroxides/hydroperoxides such as dibenzoyl peroxide, t-butyl hydroperoxide, dilauroyl peroxide, dicumyl peroxide, and mixtures thereof. According to the invention, suitable preformed peroxyacids may also include diperoxydodecandioic acid (DPDA), magnesium perphthalic acid, perlauric acid, perbenzoic acid, diperoxyazelaic acid, and mixtures thereof.

In accordance with an embodiment of the invention, one or more bleach activators, or mixtures thereof, may be used in conjunction with a peroxygen oxidant. Herein, the term bleach activators refer to compounds that react with a peroxygen oxidant such as hydrogen peroxide to form a peracid. The peracid thus formed constitutes an activated source of oxidant. The bleach activators may include compounds belonging to the class of esters, amides, imides, anhydrides, and the like. Examples of suitable bleach activators are disclosed in British Patents GB 1,586,769 and GB 2,143,231, and a method for their formation into a prilled form is described in European Published Patent Application EP-A-62,523. Examples of these bleach activators may include, but are not limited to, tetracetyl ethylene diamine (TAED), sodium 3,5,5 trimethyl hexanoyloxybenzene sulphonate, diperoxy dodecanoic acid, as described, for example, in U.S. Pat. No. 4,818, 425, nonylamide of peroxyadipic acid, as described, for example, in U.S. Pat. No. 4,259,201, and n-nonanoyloxybenzenesulphonate (NOBS). N-acyl caprolactams are also suitable and include substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam, or mixtures thereof. A particular family of bleach activators has been disclosed in EP 624,154, and the bleach activator specifically preferred in that family is acetyl triethyl citrate (ATC). Acetyl triethyl citrate has the advantage that it is environment-friendly since it eventually degrades into citric acid and alcohol. Further, acetyl triethyl citrate demonstrates substantially high hydrolytical stability during storage and is an efficient bleach activator. Another particular family of bleach activators has been disclosed in U.S. Pat. Nos. 5,741,437, 6,010,994 and 6,046,150, generally described as n-alkyl alkyl ammonium acetonitrile activators. The bleach activator particularly preferred in that family is n-methyl morpholinium acetonitrile (MMA). In accordance with various embodiments of the invention, other sources of oxidant may also include one or more bleach activators.

In accordance with various embodiments of the invention, persulfate salts, or mixtures thereof, may also be used as the source of oxidant. These persulfate salts provide active oxygen that may also be used. In accordance with an embodiment of the invention, a persulfate salt may be used in the form of monopersulfate triple salt, for example, potassium monopersulfate, which is commercialized by Peroxide Chemie GMBH under the trade name Curox®, by Degussa under the trade name Caroat, and by Du Pont under the trade name Oxone.

In accordance with an embodiment of the invention, the concentration of the source of oxidant, such as sodium hypochlorite, in the aqueous bleaching solution may be in the range of 0.001 percent to 10 percent by weight. For example, for embodiments used in laundry applications, the concentration of sodium hypochlorite in the aqueous bleaching solution may lie in the range of about 2 percent to about 7 percent. For example, for embodiments used in cleaning hard surfaces or non-porous soft surfaces, the concentration of sodium hypochlorite may lie in the range of about 0.01 to about 5 percent.

Optically Functional Nanoparticles

In accordance with an embodiment of the invention, the optically functional nanoparticles may include particles of optically functional materials such as pigments, dyes, dyestuffs, minerals, semiconductor particles, synthetic layered semiconductor particles, core-shell particles, quantum dots, fluorescent agents, phosphorescent agents, fluorescent whitening agents, ultraviolet absorbing materials, ultraviolet reflecting materials, light-absorbing materials, encapsulated colorants, or combinations thereof. These optically functional nanoparticles may be reasonably stable to oxidation. In particular, the optically functional nanoparticles may be stable to oxidation by halogen bleaches. In accordance with an embodiment of the invention, the optically functional nanoparticles may include anthroquinone derivatives.

Further, the optically functional nanoparticles may include a light absorbing material. The light absorbing material may absorb radiations like visible and ultraviolet radiations and reduce, for example, the chemical degradation of the source of oxidant and additional additives in the aqueous bleaching solution by these radiations. The optically functional nanoparticles may also include a light reflecting material to, for example, prevent the chemical degradation of the source of oxidant and additional adjuncts present in the aqueous bleaching solution. The light reflecting material may reflect the radiation such as visible, ultraviolet and infrared radiations and prevent the degradation caused by these radiations. The optically functional nanoparticles may also include, for example, fluorescent agents, phosphorescent agents, whitening agents, brightening agents, and the like. These optically functional nanoparticles may render properties such as luminescence, whitening, brightening, and similar light emission benefits, to the aqueous bleaching solution and/or the treated substrates where application enables deposition or absorption of the optically functional nanoparticles onto a receptive surface. In accordance with an embodiment of the invention, a combination of one or more of the aforementioned types of optically functional nanoparticles may be used in the aqueous bleaching solution.

In accordance with an embodiment of the invention, the optically functional nanoparticles may exhibit at least one optical absorbance band that lies within the ultraviolet portion of the spectrum so as to impart no human perceivable color to the aqueous bleaching solution within the visible spectrum.

In accordance with another embodiment of the invention, the optically functional nanoparticles may include visibly colored particles exhibiting at least one optical absorbance band, which provides a human perceivable color to the oxidant-stable polymer in solution and the aqueous bleaching solution, which lies within the visible spectrum.

Figure 2:
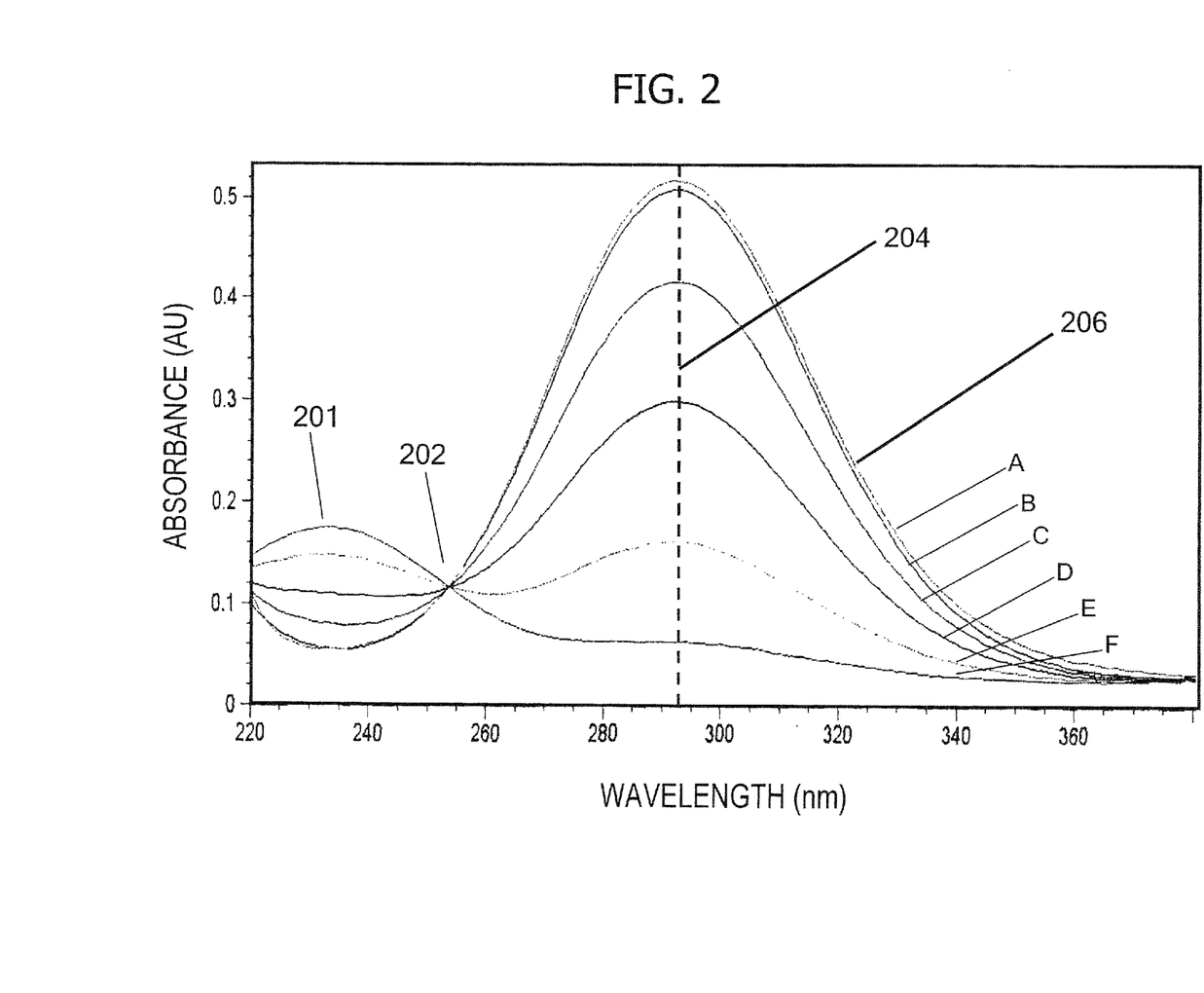
FIG. 2 is an absorbance plot versus wavelength for a representative aqueous sodium hypochlorite bleach solution at various pH values.

In accordance with a further embodiment of the invention, the optically functional nanoparticles include particles exhibiting an optical absorbance band which overlaps the optical absorbance band of the source of oxidant so as to competitively absorb the same or similar wavelengths of electromagnetic radiation (light) as the source of oxidant, so that the source of oxidant absorbs less incident radiation that it would in the absence of the optically functional nanoparticle. FIG. 2 shows typical absorbance plots of an aqueous solution of a hypohalous source, here represented by a series of dilute solutions of sodium hypochlorite in water, wherein the pH of the solution has been changed. Absorbance plot 206 corresponds to a nominal concentration of the sodium hypochlorite of about 2400 ppm (weight parts per million) in water at the normally obtained pH from dilution into distilled water, or roughly about pH 11. The remaining absorbance plots represented by plots A-F under 206 represent the same diluted solution adjusted to have correspondingly lower pH values of roughly about pH 10, 9, 8, 7 and 6, correspondingly to lines labeled "A" through "F" as indicated. Peak 204 (dotted line) represents the absorbance maximum of the hypohalous ion species, the absorbance maximum being the wavelength of light at which the species absorbs the most incident radiation, but absorbance occurs under the envelop of the absorption profile (206). A second absorbance peak 201 is seen to be particularly dominate with the lower pH bleach solutions, due to the hypohalous acid species which dominates at more acidic pH values. These two species are in equilibrium and the relative amounts of each species present change with both a change of pH and the overall concentration of the hypohalous bleach source, as evidenced by the presence of an isobestic absorbance point 202 through which the combined absorbance spectra all converge, both species being present at all concentrations and only their relative amount varying here as a function of bleach solution pH. Because the two species have different molar extinction coefficients, this being the ability of a particular species to absorb light, the relative absorbance strengths (peak height) are not necessarily indicative of the amount of the species present.

Examples of commercially available colorants suitable for use in the present invention include Lumogen® F Red 300 (red emitter), Lumogen® Red 300 Nanocolorant® (red emitter), and Lumogen® F Yellow 083 (yellow emitter), available from BASF Aktiengesellschaft of Germany. The Nanocolorant® materials from BASF are unexpectedly found to be particularly suitable for incorporation into aqueous bleaching solutions owing to the average particle sizes being significantly below 400 nm, so that the fraction of particles having larger sizes is negligable, in addition to the ability of the materials to remain stably suspended for very long periods of time without the need for a polymer dispersant or thickening of the bleaching solution. The Nanocolorant® materials are prepared by a miniemulsion polymerization process developed by BASF that produces polymer encapsulated dyestuffs that exhibit excellent resistant to bleach, the miniemulsion processing of dyestuff described by Clemens, et al, Polymer Preprints 41(1), pages 24-25 (2000), which is hereby incorporated in its entirety by reference. While the commercially available materials incorporate colored dyestuffs, other materials such as ultraviolet light absorbers, light scattering materials, fluorescent brighteners and phosphorescent materials could be used and prepared in a similar fashion to provide optically functional nanoparticles suitable for use in the present invention, where the nanoparticles would provide one or more additional optical benefits to the bleaching solutions and substrates treated with the inventive solutions apart from a visual coloring effect.

Examples of the optically functional nanoparticles may include but are not limited to mineral oxides such as cobalt aluminum oxide, zinc oxide, magnesium oxide, titanium oxide, silicon dioxide and the like, having average particle sizes below about 400 nanometers.

Further, the optically functional nanoparticles may also include one or more fluorescent whitening agents (FWA) prepared in any suitable means so as to provide a dispersion of nanoparticulate sized particles below an average particle size of 400 nanometers. In accordance with an embodiment of the invention, the optically functional nanoparticles may also include commercially available optical brighteners. Examples of the optical brighteners may include but are not limited to distyryl-biphenyl (DSBP) optical brighteners, which can be mono- or polysulfonated; triazinyl stilbene optical brighteners that can be mono- or polysulfonated, triazolylstilbenes optical brighteners, which can be mono- or polysulfonated, naphthotriazolyl stilbenes optical brighteners that can be mono- or polysulfonated, diarylpyrazolines and coumarins, as described in U.S. Patent Application 2003/0126689, which is hereby incorporated by reference.

Exemplar FWAs include but are not limited to stilbenic type 4,4'-bis anilino-6-[bis(hydroxyethylmethyl)amino]-s-triazin-2-yl amino 2,2'-stilbenedisulfonic acid, available as Tinopal® 5BM-GX from Ciba-Geigy; 4,4'-bis anilino-6 [bis (2,2-hydroxyethyl)amino]-2-triazin-2,2-yl amino-2,2' stilbene disulfonic acid, available as Tinopal® UNPA-GX from Ciba-Geigy; cyanuric chloride/diaminostilbene types such as Tinopal® AMS, DMS, 5BM, and UNPA from Ciba-Geigy Corp. and Blankophor® DML from Mobay; and the distyryl-biphenyl types, for example, 2,2'-biphenyl-4,4'-diyl-di-2,1-ethenediyl benzenesulfonic acid and disodium salt, available as Tinopal® CBS-X from Ciba-Geigy.

While the FWA and optical brightener materials are commercially available in powder form, additional processing may be needed to reduce the particle size to the preferred nanometer size range below 400 nanometers, achievable by any suitable means including, but not limited to a mechanical or solvent precipitation process for example. As a non-limiting example, the miniemulsion polymerization process employed by BASF referenced herein would be one suitable means of providing nanoparticulate FWAs suitable for use in the present invention.

Other suitable optically functional nanoparticles include those nanoparticles selected from mineral and semiconductor crystals, and semiconductor quantum dots. In contrast to bulk semiconductors which display a rather uniform absorption spectrum, the absorption spectrum for quantum dots appears as a series of overlapping peaks that get larger at shorter wavelengths. The dots will not absorb light that has a wavelength longer than that of the first exciton peak, also referred to as the absorption onset. Like all other optical and electronic properties, the wavelength of the first exciton peak (and all subsequent peaks) is a function of the composition and size of the dot. Smaller dots result in a first exciton peak at shorter wavelengths. Quantum dots may also exhibit a broad band absorption region below the first excitation band that acts as an effective broadband cut-off filter with respect to a radiation source in the visible and near visible wavelengths of light corresponding in wavelength to within one or two orders of magnitude of the actual physical dimensions of the dot material expressed in nanometer units of measurement.

A quantum dot is a crystal of semiconductor compound, including for example, but not limited to compounds of CdSe, PbS, GaAs, InGaP, ZnS, ZnSe, ZnTe, CdS, CdTe, HgS, HgSe, HgTe, MgS, MgSe, MgTe, CaS, CaSe, CaTe, SrS, SrSe, SrTe, BaS, BaSe, BaTe, GaN, GaP, GaSb, InN, InP, InAs, In, Sb, Ge, Si, and alloys or mixtures thereof; having a diameter on the order of the compound's exciton Bohr radius, corresponding to quantum dots of between 1 and 400 nanometers wide (10 to 50 atoms to about 50-1,000 atoms of a semiconductor compound), being of a size where quantum effects predominate to produce a range of useful electrical and optical properties that diverge in character from those of bulk material. Also suitable are core/shell materials comprising a core crystal of one type of semiconductor material surrounded by a shell material comprising a different semiconductor material and/or protective coating material, alloy, mixture or compound that has at least one atom differing from the core material comprising the quantum dot.

In one embodiment of the present invention, a plurality of quantum dot is employed which exibit an absorbance band between 250 to 400 nanometers corresponding to the absorbance maximum of an aqueous hypohalous and/or hypohalite species present in a bleaching solution.

In another embodiment of the present invention, an aqueous solution contains an oxidant and a plurality of quantum dots that are visibly colored nanoparticles exhibiting at least one optical absorbance band providing a human perceivable color to the aqueous solution that lies within the visible spectrum of about 300 to 800 nanometers wavelength.

For use in aqueous bleaching solutions of the present invention, quantum dots and core/shell quantum dot materials may be used at any sufficient level required to impart the desired optically functional benefit to either the aqueous solution, and/or a substrate treated with the aqueous solution whereby quantum dots are delivered to a surface of the substrate. In aqueous bleaching solutions, levels of between 0.0001 percent by weight to about 5 percent by weight, or from between 0.001 to about 1 percent by weight, or less than about 0.1 percent by weight of a plurality of quantum dot and or core/shell quantum dot material may be present in the bleaching solution.

The optically functional nanoparticles may also be selected from nanoparticles comprising materials selected from $Co_xAl_yO_z$, $Co_xB_yO_z$, $Co_xZn_yO_z$, $Co_xZn_yB_zO_w$, $Co_xZn_ySi_zO_w$, $Co_xCr_yO_z$, $Co_xMg_yB_zO_w$, chrome antimony titanium buff rutile, chrome tungsten titanium buff rutile, cobalt aluminate blue spinel, cobalt chromite spinel, cobalt nickel zinc titanium spinel, copper manganese chromite black spinel, chromium oxide, manganese antimony chromite titanium buff rutile, manganese zinc chromate spinel, nickel antimony titanium rutile, nickel tungsten rutile, zinc chrome cobalt aluminate spinel, titanium dioxide, zinc oxide, cerium oxide, magnesium oxide, and mixtures thereof; wherein x, y, z and w are integers having independently selected values of between 1 to about 10.

Further, the optically functional nanoparticles may be of a predetermined particle size. In accordance with an embodiment of the invention, the average particle size may be in the range of 0.1 nanometers to 400 nanometers. In particular, the average particle size may be in the range of 1 nanometer to 100 nanometers. Alternatively, the average particle size may be in the range of 5 nanometers to 50 nanometers.

In accordance with various embodiments of the invention, the optically functional nanoparticles are substantially stable in the aqueous bleaching solution and remain suspended in the aqueous bleaching solution due to their substantially small size. Commercial sources of pigments, colorants, dyestuffs and the like may be suitably employed in the present invention provided that they are screened to isolate the desired fraction of nanoparticles having the requisite average particle size requirement for suitable dispersability, or are process in some manner so as to reduce the average particle size to the required range. Further, the optically functional nanoparticles may be oxidatively stabilized to enhance the stability of the aqueous bleaching solution by any means available in the art, including but not limited to mineral coatings, polymeric coatings, surfactant coatings and the like.

In accordance with an embodiment of the invention, the aqueous bleaching solution may include more than one type of the optically functional nanoparticles mentioned above.

Further, the total concentration of the optically functional nanoparticles in the aqueous bleaching solution may be in the range of about 0.0001 to about 5 percent by weight.

In accordance with another embodiment of the invention, the optically functional nanoparticles provide uniform optically functional properties to the aqueous bleaching solution. Optically functional benefits provided to the aqueous bleaching solution include uniform light absorption, light and radiation scattering, fluorescent emission, phosphorescent emission, coloration, and visual aesthetics and the like. Further, optically functional benefits include those provided to a substrate or surface treated with the aqueous bleaching solutions of the present invention whereby the optically functional property is transferred either temporarily or permanently to the substrate or surface following contact with the bleaching solutions.

For use in aqueous bleaching solutions of the present invention, optically functional nanoparticles may be used at any sufficient level required to impart the desired optically functional benefit to either the aqueous solution, and/or a substrate treated with the aqueous solution whereby one or more optically functional nanoparticles are delivered to a surface of the substrate. In aqueous bleaching solutions, levels of between 0.0001 percent by weight to about 5 percent by weight, or from between 0.001 to about 1 percent by weight, or less than about 0.1 percent by weight of a plurality of optically functional nanoparticle may be present in the bleaching solution.

In accordance with an embodiment of the invention, the compositions containing optically functional nanoparticles may also optionally include one or more non-optically functional particles. The non-optically functional particles, if present, have functions other than providing an optical benefit to either the composition or a substrate treated with the composition. Examples of these functions may include, but are not limited to, thickening, abrasive and dispersive functionality, and the like, being either functional with regards to the composition or with regard to a substrate treated with the composition, but not including the imparting of any particular optical benefit thereto. In accordance with an embodiment of the invention, the average density of the non-optically functional particles may be the same or different from that of the aqueous bleaching solution. Further, the average particle size of the non-optically functional particles may be in the range of about 500 nanometers to about 1000 microns, alternatively from about 500 nanometers to about 500 microns. In one embodiment of the invention, the non-optically functional particles are present to provide a non-scratching abrasive function to the composition when applied and wiped onto a glossy substrate, wherein the non-optically functional particles are abrasive particles having an average particle size of between 50 to 250 microns.

In accordance with an embodiment of the invention, the oxidant-stable surfactants may include organic synthetic surface-active agents for cleaning and emulsification. Examples of these surfactants include but are not limited to well-known synthetic anionic, nonionic, amphoteric and zwitterionic surfactants. In particular, alkyl benzene sulfonates, alkyl and alkylether sulfates, paraffin sulfonates, olefin sulfonates, alkyl disulfonates and polysulfonates, alkoxylated alcohols and alkyl phenols, amine oxides, alpha-sulfonates of fatty acids and of fatty acid esters, alkyl betaines, and the like, may be used. These surfactants may be used, for example, in the form of their sodium, potassium, ammonium or triethanolammonium salts. The surfactants are exemplified in McCutcheon's Emulsifiers and Detergents (1994) and Kirk-Othmer Encyclopedia of Chemical Technology 3rd, Vol. 22, "Surfactants," pp. 332-432 (1983), both of which are incorporated herein by reference.

In accordance with an embodiment of the invention, the oxidant-stable surfactants may comprise up to 30 percent of the aqueous bleaching solution. In particular, the concentration of the oxidant-stable surfactants may be in the range of about 0.1 percent to about 20 percent by weight of the aqueous bleaching solution. Alternatively, the concentration of oxidant-stable surfactants may be in the range of about 0.5 percent to 10 percent by weight.

In accordance with an embodiment of the invention, the oxidant-stable polymers may be used to further stabilize the optically functional nanoparticles in the aqueous bleaching solution. These oxidant-stable polymers may be formed, for example, by the polymerization of one or more hydrophobic monomers in combination with one or more hydrophilic monomers. Examples of the monomers that may be used include but are not limited to acrylic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N— vinylsuccinamidic acid, mesaconic acid, methacroylalanine, acryloylhydroxyglycine, sulfoethyl methacrylate, sulfopropyl acrylate, sulfoethyl acrylate, and combinations thereof.

In accordance with an embodiment of the invention, the optically functional nanoparticles may be associated with the oxidant-stable polymers. In particular, the hydrophobic portions of the optically functional nanoparticles and the oxidant-stable polymers may become associated, enabling the optically functional nanoparticles to remain suspended for increased duration and under more extreme variations in storage conditions (such as freezing and thawing) owing to hydrophilic monomers present in the oxidant-stable polymers that act to couple the polymer associated nanoparticles with the aqueous bleaching solutions of the present invention.

In accordance with an embodiment of the invention, the aqueous bleaching solution may also include one or more cleaning actives to enable a desired performance. Examples of these cleaning actives may include surface-active agents, anti-corrosion agents, and the like. The cleaning actives may also include surfactants, builders, pH control agents, pH-buffering components, chelants, sequestrants, stabilizing agents, brighteners, fillers, binding agents, anti-dusting agents, dispersing agents, co-surfactants, and aesthetic adjuncts such as fragrances, coloring agents, dyes, whiteners, solvents and chelating agents, which contribute to the aesthetic appeal of the compositions. Further, the aqueous bleaching solution may also include one or more opacifiers. The use of opacifiers may reduce the number of optically functional nanoparticles needed to provide a color to the aqueous bleaching solution.

In accordance with an embodiment of the invention, the aqueous bleaching solution may optionally include an alkalinity source. The alkalinity source may be a builder, a buffer, a pH-adjusting agent, and the like. The alkalinity source may be used to increase the effectiveness of the oxidant-stable surfactant and the overall cleaning efficiency of the aqueous bleaching solution. The alkalinity source may also function as a water softener and a sequestering agent in the aqueous bleaching solution. The builder, buffer and pH-adjusting agents may also be used alone, in mixtures, in combination with or in the form of their appropriate conjugate acids or conjugate bases, to adjust and control the pH of the aqueous bleaching solution. In accordance with an embodiment of the invention, the pH of the aqueous bleaching solution containing sodium hypochlorite as the source of oxidant may be in the range of about 7 to about 13.5. In particular, the pH may be above about 11.

In accordance with an embodiment of the invention, the aqueous bleaching solution may have substantially low viscosity. In accordance with an embodiment of the invention, the viscosity of the aqueous bleaching solution may be less than 100 MilliPascal seconds (mPa·s) at 25 degrees Celsius (° C.). In particular, the viscosity of the aqueous bleaching solution may be less than 10 MilliPascal seconds (mPa·s) at 25° C.

In accordance with an embodiment of the invention, aqueous bleaching solutions with sodium hypochlorite as the source of oxidant may include at least an equimolar concentration of sodium chloride. Further, sodium carbonate, sodium hydroxide and other buffering agents may also be included in the aqueous bleaching solutions. Inorganic salts such as sodium sulfate and sodium borate may also be present. Moreover, sodium silicates may be used to stabilize the pH and reduce the corrosion effect of the aqueous bleaching solution.

It should be noted that the main ingredient in the aqueous bleaching solution is water, which may be softened, distilled or de-ionized. Water provides the continuous liquid phase into which the other ingredients are dissolved or dispersed. The amount of water present in the aqueous bleaching solution may exceed about 30 percent, and may be as high as about 99.9 percent. In particular, water is present in a quantity that is sufficient to provide appropriate rheological characteristics.

In accordance with an embodiment of the invention, the aqueous bleaching solution described in the sections mentioned above may be included in a kit. The kit may also include a plurality of non-optically functional particles. The non-optically functional particles may be characterized such that the average density of the non-optically functional particles is either the same or different from that of the aqueous bleaching solution, and the average particle size of the non-optically functional particles is between about 500 nanometers to about 1000 microns. Further, the non-optically functional particles may be substantially stable in the aqueous bleaching solution. The kit may also include instructions for using the aqueous bleaching solution. In particular, the kit may include instructions for preparing an aqueous wash liquor by using the aqueous bleaching solution, and also for applying the aqueous bleaching solution to a substrate. Moreover, the kit may also include packaging material containing the aqueous bleaching solution.

Methods of Use

Methods of use of the present invention include all such means whereby an aqueous bleaching solution may be prepared and used, to provide an improved bleaching performance.

The method of preparation of the aqueous bleaching solution includes adding the optically functional nanoparticles to an aqueous solution of the source of oxidant. The method may also include adding an oxidant-stable polymer, which may be formed by polymerizing one or more reactive monomers. These reactive monomers may include one or more hydrophobic monomers. The reactive monomers may also include one or more hydrophilic monomers. In accordance with an embodiment of the invention, the reactive monomers include at least one polymerizable ethylene group and one or more carboxylic groups. In accordance with an embodiment of the invention, a concentrated aqueous dispersion of the oxidant-stable polymer is formed and added to the aqueous bleaching solution containing the optically functional nanoparticles. The aqueous bleaching solution formed by the method mentioned above has a pleasing color or appearance, and is stable for a substantially long period. In another embodiment of the invention, the presence of the oxidant-stable polymer increases the storage time of the bleaching solutions with relatively higher amounts of the optically functional nanoparticles present without requiring substantial thickening or modification of the rheology of the bleaching solutions, so that they remain easily poured and dispensed even from convention spray pumps.

Figure 1:
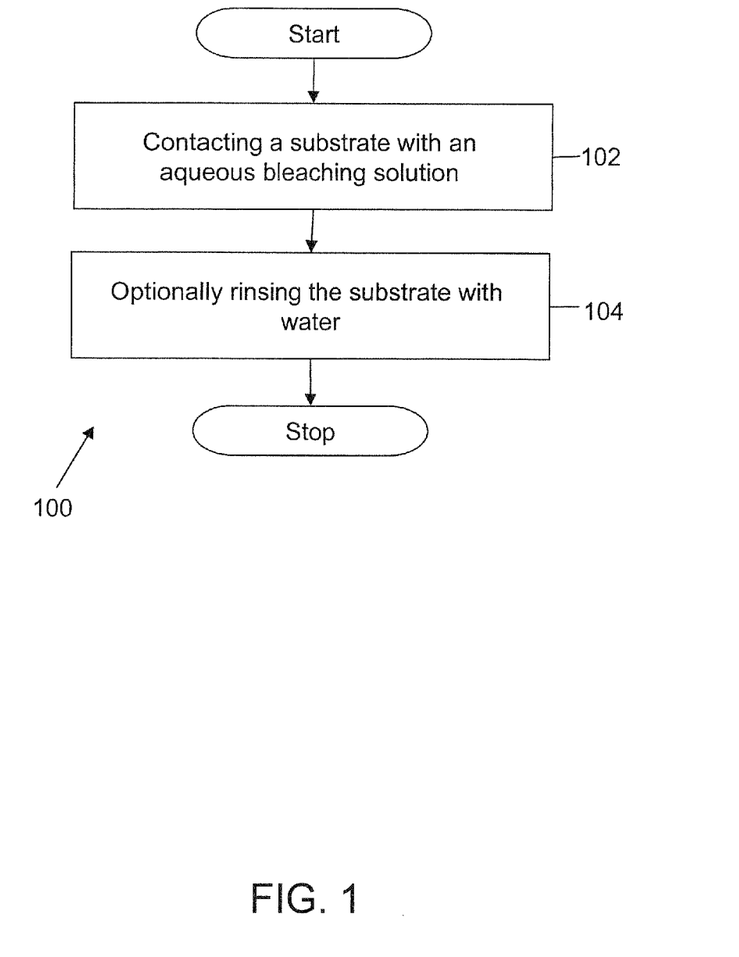
FIG. 1 is a flowchart depicting a method for treating a substrate with an aqueous solution.

FIG. 1 is a flowchart depicting a method for treating a substrate with the aqueous bleaching solution of the present invention having plurality of optically functional nanoparticles present. At step 102, the substrate is contacted with the aqueous bleaching solution, which may be the aqueous bleaching solution mentioned in earlier sections above. At step 104, the aqueous bleaching solution may be rinsed with water. In accordance with an embodiment of the invention, step 104 may be optional. In accordance with another embodiment of the invention, a removal step 104 may be done by wiping the surface of the substrate with an article, such as for example a paper towel, sponge or cloth, so that the aqueous bleaching solution is removed but a substantial number of the optically functional nanoparticles remains behind on the treated surface so as to provide that surface with some optical functionality owing to the deposited or remaining nanoparticles. In yet another embodiment, step 104 is preceded by an intermediate step 103, wherein an aqueous bleaching solution applied in step 102 is allowed to contact the substrate and dry upon a surface of the substrate whereby the intermediate step enables the deposition of a substantial number of the optically functional nanoparticles onto the treated surface. Optionally, step 104 can then be conducted in a further embodiment following intermediate step 103 to either remove excess materials (such as adjunct materials present in the aqueous bleaching solution) deposited by the application of the aqueous bleaching solution in a first step 102 without substantially removing any deposited nanoparticles, or in yet another embodiment step 104 can be conducted in such a manner as described above to remove all deposited materials including excess materials as well as the optically functional nanoparticles from the treated surface of the substrate.

In accordance with an embodiment of the invention, the aqueous bleaching solution may be used for purposes such as to effect bleaching, oxidation of stains, soils and residues, cleaning, whitening, disinfection, odor control, and sanitizing and sterilizing of soft or hard surfaces. Examples of the soft surfaces may include fabrics, textiles, clothing, rugs, and the like. In accordance with an embodiment of the invention, the aqueous bleaching solution may be a substantially dilute solution. Further, the dilute aqueous bleaching solution may include a substantially low polymer-to-pigment ratio to avoid staining of the soft surfaces. In accordance with another embodiment of the invention, the aqueous bleaching solution may include a substantially high polymer-to-pigment ratio. In accordance with an embodiment of the invention, the polymer-to-pigment ratio may be about 1000:1 to about 1:1000, or alternatively from 100:1 to about 1:100, or yet alternatively from between 10:1 to about 1:10.

Further, the aqueous bleaching solution may be a substantially concentrated solution. The aqueous bleaching solution may be rinsed with water and may be used for purposes that may include, but are not limited to, soaking and pretreating of the soft surfaces in a laundering process. The aqueous bleaching solution may also include one or more additives such as fluorescent whitening agents and brighteners to prevent yellowing of the soft surfaces.

Examples of hard surfaces may include counter tops, toilets, bathroom surfaces, floors, metal surfaces, wooden surfaces, and the like. The aqueous bleaching solution may be a substantially concentrated solution. In accordance with an embodiment of the invention, the aqueous bleaching solution may include a high surfactant-to-bleach ratio for cleaning of the hard surfaces. Further, the aqueous bleaching solution may be optionally rinsed with water.

Experimental

Experiments were carried out to test the stability of aqueous bleaching solutions containing various optically functional nanoparticles. Table 1 shows several embodiments of the invention using commercial nanopigments and nanocolorants in bleaching compositions based on sodium hypochlorite.

Compositions generally show good stability of the hypochlorite bleach over time, showing that the selected optically functional nanoparticles do not significantly interact with the oxidant. Composition 7 is one embodiment of a fully formulated composition also containing an opacifier that renders a pastel opaque coloration to the bleach solution, in addition to other adjuncts. Composition 7 further provides an example of one embodiment of the invention useful as a laundry bleach for treating textile substrates, where the optically functional nanoparticles are selected to have no binding affinity for a textile substrate, so that there would effectively be no nanoparticles remaining on the textile after the washing process is complete, usually being a final water rinse to remove detergent, bleach or a laundry additive such as Composition 7 in place of the bleach additive. Composition 7 also represents one embodiment featuring an opacifier. An opacifier, by effectively scattering incident light and radiation in all directions, is believed, without being bound by theory, to act in a manner that improves the ability of the optically functional nanoparticulates added for light absorption benefits by preventing the penetration of the incident light into the bulk aqueous solutions of the invention. Compositions 1-6 are embodiments of dilute bleach solutions suitable for hard surface cleaning and disinfection, including spray applications where the bleach solutions are applied to a surface. Addition of a polymer dispersant is optional, but appears to provide additional dispersion stability of the optically functional nanoparticles in the bleach solutions for prolonged storage and resistance against aggregation, separation and precipitation. Composition 8 is an embodiment of a deeply colored concentrated bleach solution that would be particularly efficacious in having the optical characteristic of being easily detectable when present on a surface, such as for example, when spilled or applied onto a surface, so that a person would readily perceive where a spill has occurred or what portion of the surface has been exposed to the inventive bleaching composition, respectively. The concentrated compositions 7 and 8 are particularly exemplary embodiments suitable for dilution for use in a washing machine for laundry treatment, whereby the colored bleach solution enables better visual measurement of the dosing level by providing a more clearly discernable meniscus against the wall of a measuring cup or dosing cap prior to dilution. Densities of the optically functional materials present in the exemplary embodiments range from about 1.27 to about 4.4 g/cm$^3$.

TABLE 1

| Ingredient | Composition | | | | | | | |
|---|---|---|---|---|---|---|---|---|
| | 1 | 2 | 3 | 4 | 5 | 6 | 7 | 8 |
| Sodium Hypochlorite | 0.008 | 0.008 | 0.01 | 0.250 | 1.0 | 1.0 | 3.2 | 6.0 |
| Sodium Hydroxide | | | | | | | 1.25 | 0.75 |
| Anionic Surfactant (1) | | | | | | | 2.1 | |
| Soap (2) | | | | | | | 0.1 | |
| Sequestrant (3) | | | | | | | 0.1 | |
| Polymer dispersant (4) | | | 0.05 | | | | 0.05 | 0.1 |
| Opacifier (5) | | | | | 0.25 | 0.25 | 0.12 | 0.5 |
| SG-MB215-SWC (6) | 0.5 | | | 0.05 | | 0.10 | | 0.75 |
| SB-MB215-SVZG (7) | | 0.5 | 0.5 | | 0.10 | | | |
| Lumogen ® Nano-colorant ® (8) | | | | | | | 0.5 | 2.0 |
| Water (to 100%) | q.s. | q.s. | q.s. | q.s. | q.s. | q.s. | q.s. | q.s. |
| pH (9) | 7.5 | 7.5 | 5.1 | 8.0 | 9.5 | 9.5 | 12.8 | 12.0 |

(1) Fatty Alcohol ether sulfate with nominal C12 to C14 alkyl chain length and two moles ethoxylate.
(2) Potassium Cocoate—Potassium salt of carboxylic acid soap derived from Coconut oil.
(3) Sequion ® CLR, a potassium salt of N-oxide derivative of amino(tri(methylenephosphonic acid)) (ATMP), available from Giovanni Bozzetto S.p.A., Italy.
(4) Acusol 470 N, a modified polyacrylate modified polycarboxylate available from Rohm & Haas, Philadelphia, PA, U.S.A.
(5) Acusol OP 301, a nominal styrene-acrylic copolymer available from Rohm & Haas.
(6) Cobalt aluminate (CoAl$_2$O$_4$) nanopigment coated with polyethylene sulfone having an average particle size of 100 nm, available from Sukgyung AT (Korea), Des Plaines, IL, U.S.A.
(7) Zinc oxide (zirconium) coated cobalt aluminate (CoAl$_2$O$_4$) nanopigment with average particle size of 100 nm, available from Sukgyung AT.
(8) Nanocolorant polymer-dye complex having an average particle size of less than about 400 nm, available from BASF, Ludwigschaffen, Germany. Density of the Lumogen series nanocolorants is around about 1.27 g/cm$^3$.
(9) pH obtained through dilution of a concentrated stock solution of approximately 6.0% sodium hypochlorite as Clorox ® Liquid Bleach, available from the Clorox Company, Oakland, CA, U.S.A. Adjusted with sodium hydroxide as required.

Table 2 shows a series of compositions representing embodiments of the invention employing the nanopigments at various solution pH's to determine the effective range. For hypochlorite bleach, longer storage stability is generally favored by higher pH's in the alkaline range, although lower pH's at and around neutral can also be employed if purified water and materials are employed. In Table 2, a commercial bleach solution was diluted to produce a stock solution, which was then dosed with the indicated nanopigments and the pH adjusted. Compositions 9-14 showed excellent stability as to the maintenance of uniform color to the bleaching solutions characteristic of the nanoparticulate for over 24 hours at ambient (room temperature) storage, with no change in appearance. At higher pH, however, the particular nanopigments employed tended to either aggregate and/or precipitate from solution before 24 hours, although no immediate changes in appearance were noted in the first several hours following preparation. Bleach activity did not appear to be effected by the presence of the nanopigments, suggesting that at higher pH's these particular nanopigments would likely be suitable for use for shorter times, or alternatively could be further stabilized by addition of a polymer or surfactant dispersant. Without being bound by theory, it is believed that at the higher pH that ionic strength effects might be dominating the system, since no reaction between the materials and the oxidant was noted, in that the color of the materials was not effected and were redispersible upon gentle shaking of the solutions. A test composition 16 free of sodium hypochlorite but adjusted to a high pH also exhibited some aggregation and precipitation demonstrates that any change at high pH is not due to the presence of the bleach, but rather likely being due to the overall ionic strength of the solution.

TABLE 2

| Ingredient | Composition | | | | | | | |
|---|---|---|---|---|---|---|---|---|
| | 9 | 10 | 11 | 12 | 13 | 14 | 15 | 16 (4) |
| Sodium Hypochlorite (1) | 0.83 | 0.83 | 0.83 | 0.83 | 0.83 | 0.83 | 0.83 | -0- |
| SB-MB215-SVZG | 0.05 | 0.05 | 0.05 | 0.05 | | 0.05 | | 0.05 |
| SB-MB215-SWC | | | | | 0.05 | | 0.05 | |
| Water (to 100%) | q.s. | q.s. | q.s. | q.s. | q.s. | q.s. | q.s. | q.s. |
| pH (2) | 5.5 (3) | ~9 | ~10 | ~11 | ~11 | ~12 | ~12 | ~14 |
| Appearance @ 24 hrs Room Temperature (5) | S | S | S | S | S | S | U | U |

(1) Clorox ® Liquid Bleach as stock solution diluted with distilled water to indicated wt. % active.
(2) The pH was adjusted to approximate value indicated by dropwise addition of a 50% sodium hydroxide solution to a prepared solution of diluted sodium hypochlorite bleach with nanopigment present.
(3) Solution pH upon dilution of bleach stock. No sodium hydroxide added.
(4) Control composition containing no bleach.
(5) Visual observation following storage conditions: S = Stable for over 24 hrs with no change in appearance; U = Unstable, aggregation and/or precipitation noted within 24 hrs.

Table 3 lists some properties and the densities (most references provide this measurement as the "specific gravity" being the relative density of a material compared to that of pure water at standard conditions of temperature and pressure, "STP") of a variety of metal oxides and intermetallic oxides including common rutile and spinel minerals that are suitable for use as nanoparticulates in the present invention. These particular materials are crystalline in nature, extremely stable against heat and oxidation, and have a variety of colors representative of characteristic absorbance's in the visual spectrum. Densities of these materials range from above about 4 to about 7 g/cm$^3$, although the value can vary depending on the form and crystallographic configuration (rutile or spinel for example), as well as the source of the material. The cerium oxide and zinc oxide materials are commercially available from Degussa in the form of nanoparticulates immediately suitable for use in bleaching solutions of the present invention. These are two representative examples of nanopigments that provide an optical function benefit by absorbing incident ultraviolet radiation in the UV-A and/or UV-B when used alone or in combination in the inventive bleaching solutions, and/or substrates to which the bleaching solutions containing the optically functional nanoparticles are applied.

The other pigments are commercially available, but require size screening to eliminate larger particles or further reduction of the average particle size to obtain nanoparticles having an average particle size below about 400 nanometers before incorporation into the inventive bleach solutions as optically functional nanoparticles.

TABLE 3

| Pigments | Color (C.I.) (1) | Density (g/cm$^3$) |
|---|---|---|
| Cerium oxide (2) | — | 6.77 |
| Chrome Antimony Titanium Buff Rutile (3) | Yellow (77310) | 4.46 |
| Chrome Tungsten Titanium Buff Rutile (3) | Orange (77897) | 4.44 |
| Cobalt Aluminate Blue Spinel (3) | Cobalt Blue (77346) | 4.39 |
| Cobalt Chromite Spinel (3) | Blue-Green (77343-) | 4.37 |
| Cobalt Nickel Zinc Titanium Spinel (3) | Green (77377) | — |
| Copper Manganese Chromite Black Spinel (3) | Blue-Black (77428) | 5.33 |
| Chromium Oxide Green (3) | Green (77288) | 5.23 |
| Manganese Antimony Titanium Buff Rutile (3) | Yellow (77899) | 4.72 |
| Manganese Zinc Chromite Brown Spinel (3) | Brown (77312) | 4.92 |
| Nickel Antimony Titanium Rutile (3) | Golden Yellow (77788) | 4.61 |
| Nickel Tungsten Yellow Rutile (3) | Bright Yellow (77902) | 4.64 |
| Titanium Dioxide (TiO$_2$) | White (77891) | 4.2 |
| Zinc Oxide (4) | White (77947) | 5.6 |
| Zinc Chrome Cobalt Aluminate Spinel (3) | Cerulean Blue (77343) | 4.60 |

(1) C.I. Industry standard "Color Index" number.
(2) CeO$_2$ available in nanoparticulate size from Degussa, under the tradename AdNano ® Ceria, a strong UV-B absorber.
(3) All pigment stock available from Stochem, Edmonton, AB, Canada. Further particle size reduction or screening may be required to remove particle sizes >400 nm.
(4) Available in nanoparticulate size from Degussa, under the tradename AdNano ® Zinc Oxide, a strong UV-A filter.

Table 4 lists examples of additional nanopigments suitable for use in the inventive compositions, derived from cobalt (II) and cobalt (II) intermetallic oxides obtained via a combustion synthesis technique that yields extremely fine nanopigment forms of the materials in a wide variety of colors. Densities of the materials obtained in a combustion synthesis are typically lower than mined materials, likely owing to the reduced crystallinity of the materials obtained by pyrolysis. Further, cobalt materials are idiochromatic (self-colored) pigments that produce color owing to transition metal ions having energy absorption bands whose colors depend on the ligand and the coordination geometry, and thus produce color differently than allochromatic pigments that generate color effects by perturbation of a crystal field lattice energy by either substitution or inclusion effects of a metal ion, such as how chromium ions produce the intense red color for the ruby gemstone which is otherwise primarily quartz crystal.

TABLE 4

| Nanopigments (1) | Color | Density (g/cm$^3$) | Primary Particle Size (nm) (2) |
|---|---|---|---|
| $CoAl_2O_4$ | Indigo | 2.32 | 100 |
| $Co_2Al_{2-x}O_3$ | Blue | 2.75 | 220 |
| $Co_2B_2O_5$ | Purple | 1.85 | 270 |
| $CoZnB_4O_7$ | Violet | — | — |
| $CoZn_2SiO_4$ | Lavender | — | — |
| CoZnO | Green | — | — |
| $CoCr_2O_4$ | Blue-Green | — | — |

TABLE 4-continued

| Nanopigments (1) | Color | Density (g/cm³) | Primary Particle Size (nm) (2) |
|---|---|---|---|
| CoMg₂B₂O₅ | Rose-Pink | — | — |
| Co$_x$Mg$_{2-x}$B₂O₅ | Pink | 2.1 | 350 |

(1) Combustion synthesized pigments described by Mimani, et al. (Current Science, Vol 78 (7), Apr. 10, 2000, 892-896), which is incorporated herein by reference in its entirety.
(2) Calculated from surface area.

Table 5 lists the properties of one exemplar embodiment being a common semiconductor based nanoparticulate, cadmium selenide, known as a "quantum dot." Quantum dot materials owe their optical properties to the crystalline nature of the material and the extremely small sizes where quantum electronic effects are exhibited with respect to selected energy states of allowed transitions for absorption and emission of light, thus producing extremely narrow emission spectra so as to provide for intense and vibrant colors. Here, the CdSe crystal is the "core" with the ZnS acting as a "shell" or coating which surrounds the core crystal material.

The quantum dots may be employed directly or versions having a further coating material to improve water solubility or dispersability may also be employed in the inventive compositions. The materials are physically stable and chemically resistant to oxidation, which combined with their small size and availability in both coated and uncoated versions render them suitable for use in the inventive compositions as optically functional nanoparticles capable of providing light absorbing and luminescent optical properties and similar benefits to the solutions and treated substrates. Owing to the large quantum yields, being the efficiency of the quantum dots to convert one wavelength of incident light to a second wavelength of emitted light, only small amounts of these material need be employed to produce colored bleaching solutions having a color or emission visible to the human eye.

TABLE 5

| Quantum Dot (1) | Maximum Emission Peak (2) | Color | Crystal Size (3) (nm) |
|---|---|---|---|
| CdSe/ZnS Core Shell | 490 | Lake Placid Blue | 1.9 |
| CdSe/ZnS Core Shell | 520 | Adirondack Green | 2.1 |
| CdSe/ZnS Core Shell | 540 | Catskill Green | 2.4 |
| CdSe/ZnS Core Shell | 560 | Hops Yellow | 2.6 |
| CdSe/ZnS Core Shell | 580 | Birch Yellow | 3.2 |
| CdSe/ZnS Core Shell | 600 | Fort Orange | 4 |
| CdSe/ZnS Core Shell | 620 | Maple Red-Orange | 5.2 |

(1) All semiconductor QDs are available from Evident Technologies, Troy, New York. Materials exhibit high broad band absorbance below about 450 nanometers, characteristic excitation maxima, and primary emission maxima corresponding to observed color.
(2) Excitation <400 nanometers. Quantum yields vary from 30 to 50% efficiency.
(3) Core cadmium selenide nanocrystal size (estimated). Shell is optionally modified with proprietary ligand coating (a carboxyl terminated surfactant). Density of the CdSe core is about 5.81 g/cm³.

In light of the foregoing discussion, it may be concluded that the methods and compositions of the invention provide an improvement in the stability of the aqueous bleaching solutions having optically functional nanoparticles present to provide at least one or more optical benefits to the bleaching solutions, without requiring the use of conventional dispersing aids, flocculants or thickening agents.

Without departing from the spirit and scope of this invention, one with ordinary skill can make various changes and modifications to the invention to adapt it to various usages and conditions. As such, these changes and modifications are properly, equitably, and intended to be, within the full range of equivalence of the following claims.

We claim:

1. An aqueous solution for substrate cleaning comprising:
   a. about 0.001 to about 10% by weight of the aqueous solution of a source of oxidant, wherein said oxidant is sodium hypochlorite;
   b. about 0.0001 to about 5% by weight percent of the aqueous solution of a plurality of optically functional nanoparticles characterized such that
      i. the average density of the plurality of optically functional nanoparticles is greater than that of the aqueous solution with the source of oxidant present, and;
      ii. the average particle size of the plurality of optically functional nanoparticles is between 0.1 nanometers to about 400 nanometers;
   wherein said composition is concentrated and colored; and
   c. optionally, an oxidant-stable polymer;
   d. optionally, an oxidant-stable surfactant; and
   e. water;
   wherein the plurality of optically functional nanoparticles are visibly colored particles exhibiting at least one optical absorbance band providing a human perceivable color to the aqueous solution that lies within the visible spectrum of about 300 to about 800 nanometers wavelength; and
   wherein said plurality of optically functional nanoparticles are semiconductor quantum dots.

2. The aqueous solution according to claim 1, wherein said quantum dots comprise semiconductor materials selected from the group consisting of CdSe, PbS, InAs, InGaP, ZnS, ZnSe, ZnTe, CdS, CdTe, HgS, HgSe, HgTe, MgS, MgSe, MgTe, CaS, CaSe, CaTe, SrS, SrSe, SaTe, BaS, BaSe, BaTe, GaN, GaP, GaAs, GaSb, InN, InP, InAs, InSb, Ge, Si; and alloys thereof and mixtures thereof.

* * * * *